(12) United States Patent
Lai

(10) Patent No.: US 8,632,183 B2
(45) Date of Patent: Jan. 21, 2014

(54) EFFECTIVE ACUITY AND REFRACTION TARGETS

(76) Inventor: Shui T. Lai, Windermere, FL (US)

(*) Notice: Subject to any disclaimer, the term of this patent is extended or adjusted under 35 U.S.C. 154(b) by 286 days.

(21) Appl. No.: 12/947,694

(22) Filed: Nov. 16, 2010

(65) Prior Publication Data

US 2012/0120370 A1    May 17, 2012

(51) Int. Cl.
*A61B 3/02* (2006.01)
*A61B 3/00* (2006.01)
*A61B 3/10* (2006.01)

(52) U.S. Cl.
USPC ............ 351/239; 351/200; 351/205; 351/222

(58) Field of Classification Search
USPC ......... 351/200, 205, 239, 246–247, 222–223, 351/240–243, 245, 201
See application file for complete search history.

(56) References Cited

U.S. PATENT DOCUMENTS

| | | | |
|---|---|---|---|
| 5,880,814 A | 3/1999 | McKnight et al. | |
| 2004/0105073 A1* | 6/2004 | Maddalena et al. | 351/205 |
| 2005/0083485 A1 | 4/2005 | Toshima et al. | |
| 2006/0227289 A1 | 10/2006 | Hasegawa et al. | |
| 2008/0018857 A1* | 1/2008 | Koppany | 351/239 |
| 2010/0128223 A1 | 5/2010 | Blumenthal et al. | |

OTHER PUBLICATIONS

PCT Notification of Transmittal of the International Search Report and the Written Opinion of the International Searching Authority, or the Declaration, for PCT Application No. PCT/US2011/061080, report dated Apr. 17, 2012, 14 pages.

* cited by examiner

*Primary Examiner* — Dawayne A Pinkney
(74) *Attorney, Agent, or Firm* — SF Bay Area Patents, LLC; Andrew V. Smith

(57) ABSTRACT

A viewing target for a visual acuity and refraction measurement includes at least one line comprising a width dimension that is below a resolution limit width (hereinafter "RLW") of a test subject visual acuity, and an adjustable length dimension that is initially set at greater than the RLW of the test subject visual acuity. A base, at least approximately intersecting the line, has a thickness along the direction of the length of the line that is greater than the RLW of the test subject visual acuity. The length dimension of the line is adjustable in increments small enough to effectively approximate the visual acuity of the test subject by determining a shortest resolvable line and a next smaller line that is not resolvable by the test subject.

42 Claims, 4 Drawing Sheets

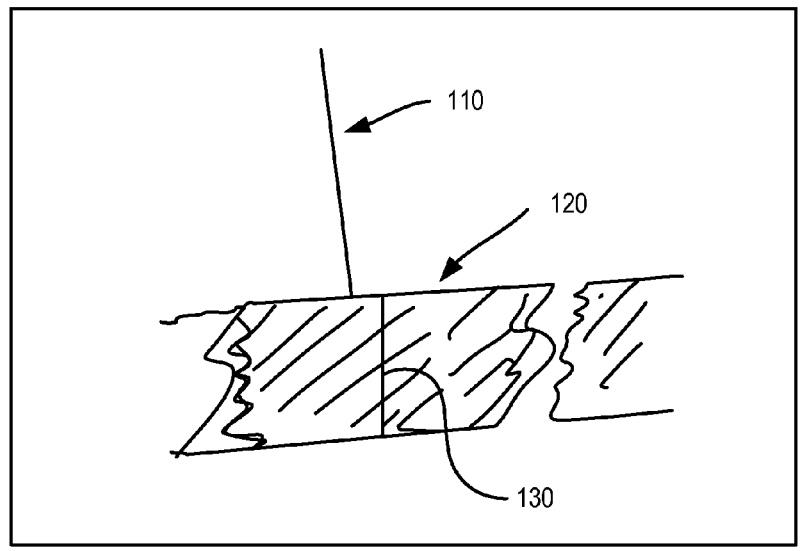
Figure 1
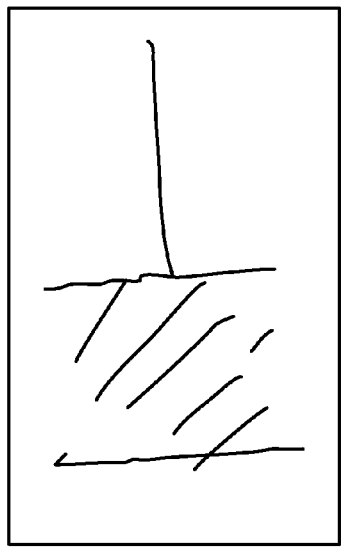 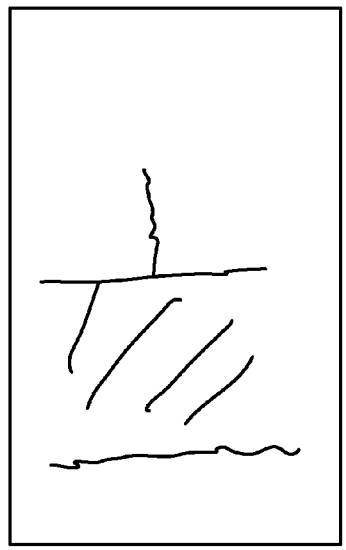 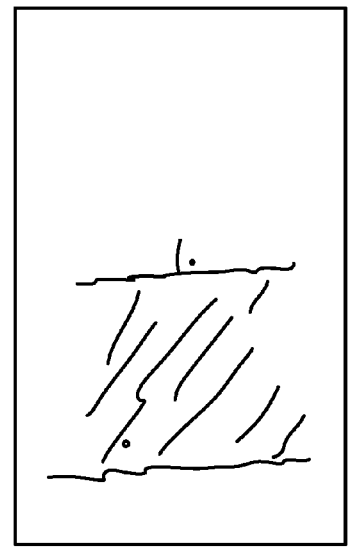
Figure 2(A)  Figure 2(B)  Figure 2(C)

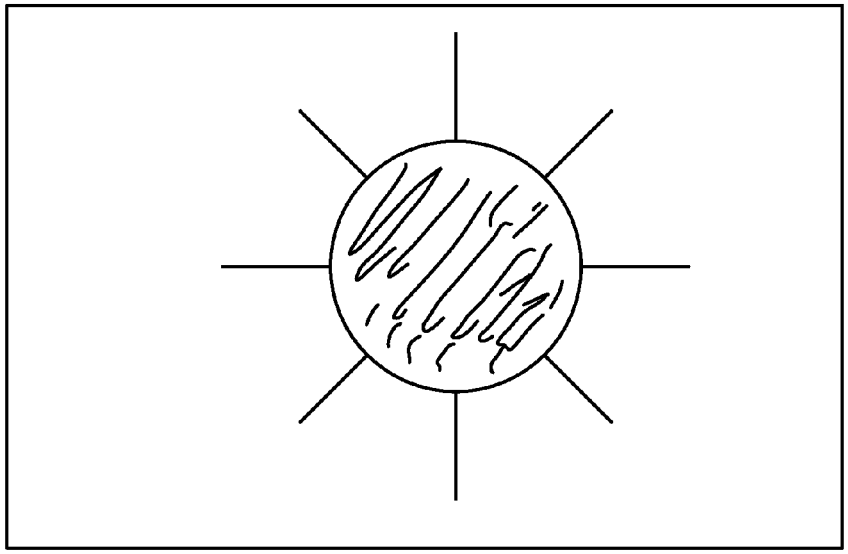
Figure 3(A)
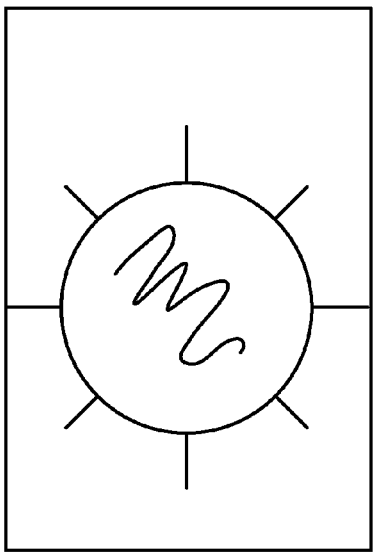 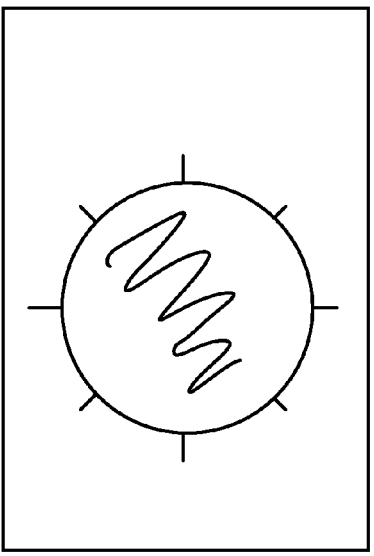 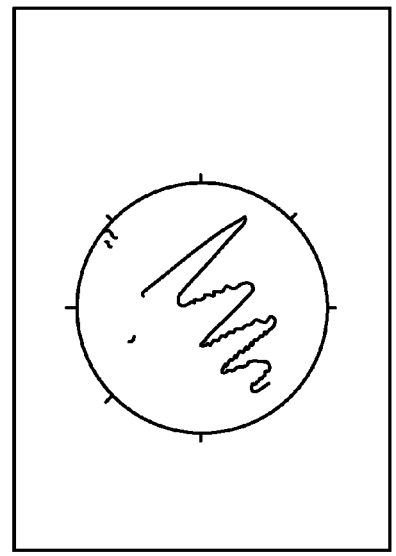
Figure 3(B)   Figure 3(C)   Figure 3(D)

EFFECTIVE ACUITY AND REFRACTION TARGETS

BACKGROUND OF THE INVENTION

The most common refraction target used by optometrists or ophthalmologists today is the Snellen letter eye chart. It consists of a list of letters typically arranged in a row, or a column. The letter size is also linked to the visual acuity level. For example, letters of font size having the height measurement of the letter N or H of 8.9 mm, it is commonly used to measure a level of 20/20 visual acuity, when such letters are placed at 20 feet away from the test subject. For the 20/10 acuity letters, the letter size is scaled by a factor of two smaller. On the other hand, the 20/40 letters would have twice the size of those of 20/20, etc.

Such eye chart is popular among eye care professional due to its low cost, easy to make, and it works for most purposes. However, a drawback of such type of eye chart is that patients can memorize the letters. Also, each letter has a different effectiveness, that is, some letters are easier than others to read. Moreover, the letters have their own intrinsic orientation. Each letter includes a certain unique configuration of "strokes" presenting a directional preference. For example, the letter H favors the vertical direction, and E has three horizontal lines and one vertical line, etc. Another drawback is that the letters are in the English language, such that the test results may differ depending on the fluency of the test subject with the English language.

Other types of eye charts include tumbling E and Landolt C. Both offer certain benefits, however, neither are used as a refraction target, because they contain only E's and C's, respectively. Therefore, both require an additional directional response to indicate if a test subject can identify the orientation of a symbol correctly. For a quick check of astigmatism, there is yet another type of chart typically used to indicate the existence of cylinder refractive error. It consists of line pairs, or thick lines, typically 12 pairs arranged in 30 degree increments, like the spokes of a wheel. A typical line width in an astigmatism chart is about 2 mm or greater. A thick line or line pairs meet at or near the center of the spoke pattern. In some cases, the spokes stop when they touch or merge with the next spoke or otherwise leave a small central blank zone. Since astigmatism refractive errors are asymmetric in nature, it causes a non-uniform appearance of the spokes, that is, some spokes appears darker than others. A conventional astigmatism chart does not provide visual acuity level information. It is hardly used as a refraction target, nor does it have the sensitivity of a Snellen eye chart when used as a refraction target.

It is desired to have a refraction target, or an eye chart, that is universally usable for all ages from child to adult, without language barriers, for literate or illiterate, convenient, low cost, and easily available to eye care professionals, as well as having no directional preference (unless it is specifically desired to test for cylinder error). Since a desired viewing target is to be used not only for acuity measurement, but also as a refraction target, to arrive at a more accurate refraction end point, it is also desired that such target exhibit higher discrimination sensitivity compared to a Snellen or letter eye chart.

BRIEF DESCRIPTION OF THE DRAWINGS

FIG. 1 schematically illustrates a viewing target including a line and a base in accordance with certain embodiments.

FIGS. 2a-2c schematically illustrate the viewing target of FIG. 1 with an adjustment line length.

FIG. 3a schematically illustrates a rotationally-symmetric viewing target including multiple lines and a circular base in accordance with certain embodiments.

FIGS. 3b-3d schematically illustrate the viewing target of FIG. 3 with adjustment line lengths.

DETAILED DESCRIPTIONS OF THE EMBODIMENTS

Figure 4A:
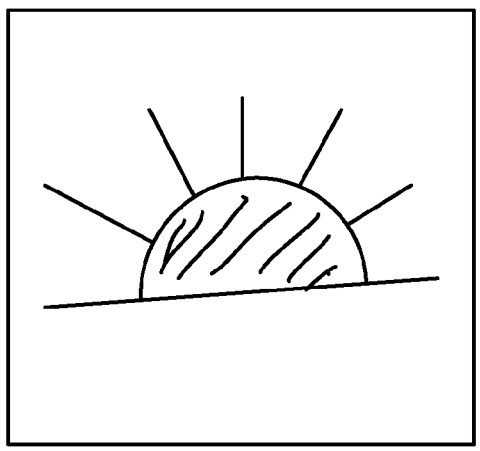
FIG. 4a schematically illustrates a viewing target in accordance with certain embodiments including a semi-circular base connected to multiple lines.

A viewing target is provided on a display for visual acuity and refraction measurements of a test subject. The viewing target includes a base and at least one line. The line has a width dimension that is below a resolution limit width (hereinafter "RLW") of a test subject visual acuity, and an adjustable length dimension that is initially set at greater than the RLW of the test subject visual acuity. The base at least approximately intersects the line, and has a thickness along the direction of the length of the line that is greater than the RLW of the test subject visual acuity. In performing a visual acuity and refraction measurement of a test subject, the length dimension of the line is adjustable in increments small enough to effectively approximate the visual acuity of the test subject by determining a shortest resolvable line and a next smaller line that is not resolvable by the test subject.

The increments of the adjustable length of the line may be as small as a single display pixel or a selected multiple thereof.

The line and the base may be white or gray color, or a combination thereof, and a background against which the target is displayed may be black color, or vice-versa.

The colors and/or grayscale characteristics and/or brightness of the line and base and background against which the target is displayed may be selectable.

The width of the line may be less than 20/10 RLW.

The length of the line may be greater than 20/40 RLW.

The thickness of the base may be equal to or greater than 20/40 RLW.

There may be a single line or multiple lines differing in their length or direction, or both.

The base may include a polygon shape and have lines protruding from it.

Five lines may protrude from the base angularly spaced at approximately equal angles apart, wherein the angles range from 2 degrees to 45 degrees.

Each of the lines may be equal in length and adjustable.

The base may have a circular shape.

The target may be adjustably elongatable for testing cylinder error.

A contrast level of the at least one line may be adjustable in a range between 1% and 100%.

The viewing target may be displayable on a computer monitor, or other electronic screen.

The base may have a circular shape, and the viewing target is adjustable for displaying in temporal increments a line protruding from the base at different angles. The different angles comprise increments between 2 degrees and 45 degrees. The temporal increments comprise 0.01 seconds to 2 seconds.

The line and base comprise a same color.

A method of determining a visual acuity level of a test subject in further provided, including reducing a length of at least one line in a viewing target until the test subject indicates that the line has disappeared into a base. The viewing target may include at least one line having a width dimension that is below a resolution limit width (hereinafter "RLW") of a test subject visual acuity, and an adjustable length dimension that is initially set at greater than the RLW of the test subject visual acuity. The base may at least approximately intersect the line, and have a thickness along the direction of the length of the line that is greater than the RLW of the test subject visual acuity. In performing a visual acuity and refraction measurement of the test subject, the length dimension of the line is adjustable in increments small enough to effectively approximate the visual acuity of the test subject by determining a shortest resolvable line and a next smaller line that is not resolvable by the test subject.

Another method of determining a refraction error includes determining a quality of an image of a line of a viewing target. The viewing target includes at least one line comprising a width dimension that is below a resolution limit width (hereinafter "RLW") of a test subject visual acuity, and an adjustable length dimension that is initially set at greater than the RLW of the test subject visual acuity. A base at least approximately intersects the line and has a thickness along the direction of the length of the line that is greater than the RLW of the test subject visual acuity. In performing a visual acuity and refraction measurement of the test subject, the length dimension of the line is adjustable in increments small enough to effectively approximate the visual acuity of the test subject by determining a shortest resolvable line and a next smaller line that is not resolvable by the test subject.

A further method is provided for determining a refraction error. The method includes reducing a length of at least one line in a viewing target until a test subject indicates that the line has disappeared into a base. The viewing target includes at least one line having a width dimension that is below a resolution limit width (hereinafter "RLW") of a test subject visual acuity, and an adjustable length dimension that is initially set at greater than the RLW of the test subject visual acuity. The base at least approximately intersects the line and has a thickness along the direction of the length of the line that is greater than the RLW of the test subject visual acuity. In performing a visual acuity and refraction measurement of the test subject, the length dimension of the line is adjustable in increments small enough to effectively approximate the visual acuity of the test subject by determining a shortest resolvable line and a next smaller line that is not resolvable by the test subject.

There may be a single line or multiple lines differing in their length or direction, or both. The base may be circular or have a polygon shape, wherein each of the lines may protrude from the base. For example, there may be five or seven lines or eight lines or more protruding from the base angularly spaced at approximately equal angles apart, wherein the angles may range from 2 degrees to 45 degrees. Each of the lines may be equal in length and adjustable. The target may be adjustably elongatable. An example of an elongated target is to take FIG. 3(A) and to change its aspect ratio along either the x, or the y direction, such that the elongation is along x or y axis in this example. Generally speaking, the elongated direction can be along any direction between zero to 180 degrees. Such elongated target can be used for testing cylinder errors.

A tangible processor-readable medium is also provided having stored therein program code for programming a processor to generate any of the viewing targets described herein on a display for visual acuity and refraction measurement of a test subject.

A visual acuity measurement system is also provided including a display for showing any of the viewing targets described herein. A machine may be coupled with the display and configured to adjust the viewing target on the display during a visual acuity and/or refraction measurement of a test subject. A calculator or look-up table, or both, may be used to determine the visual acuity of the test subject based on the visual acuity measurement.

Length Units RLW Measured in Visual Acuity Resolution Limit

An eye chart consists of letters which are arranged in rows. Letters in different rows typically have a different font size. However, such eye chart can be used at various viewing distances. The distance at which the eye chart is placed from the test subject determines the acuity level of certain letters. In other words, for a given or fixed acuity level, the length dimension of the letters in the viewing target is inherently related to the viewing distance. As an example, at 20 feet viewing distance from a test subject, a letter E with height dimension of 8.87 mm is typically used as a standard size for a 20/20 acuity level. The separation of the three horizontal lines in the letter E is to be set at about 1.77 mm, and the width of the vertical line and the horizontal lines are to be set to 1.77 mm as well, which is also the width subtended by 1 minute of arc at a distance of 20 feet, a definition of 20/20 spatial resolution. Hereby, we define a measure of spatial resolution limit in units of visual acuity. For example, 20/20 has spatial resolution limit width of 1.77 mm at 20 feet viewing distance, so a new unit 20/20 RLW means 1.77 mm when the target is placed at 20 feet viewing distance. This newly defined length unit is used throughout the rest of this specification. In another example, if the viewing distance is changed to 10 feet, the 20/20 RLW then corresponds to 0.89 mm. If the same letter E with the height of 8.8 mm is used at 10 feet, that E letter has now changed to a standard for measuring 20/40 visual acuity level. Since refractive targets are often used to assess the visual acuity level, it is convenient to use a length dimension in the units of acuity RLW in the rest of this patent specification. Otherwise, whenever a length dimension is called out, the viewing distance would also be specified. A RLW unit has a built in function for the viewing distance, in the sense that it scales with the viewing distance, just like how a visual acuity eye chart is used. We also have the following convention: if a test subject has a visual acuity of 20/20, that subject's RLW is 1.77 mm at 20 feet viewing distance. By the same token, if the viewing target is placed at 10 feet from the test subject, a 20/20 RLW means 0.885 mm. Also, f a test subject has a visual acuity of 20/20, the RLW of this test subject is 1.77 mm at 20 feet viewing, 0.885 mm at 10 feet viewing, or 2.66 mm at 30 feet viewing, etc.

Refraction and Acuity Measurement

Refracting a test subject involves finding or identifying the correct end points for the sphere, cylinder, and/or the axis orientation that would provide the best possible corrected vision. Therefore, it is desired to determine the effect on the vision of any residual refractive error in any one of the three key refraction end points. Spherical errors typically induce a symmetrical blur of any part of an image. A pure cylinder error, however, has a preferential direction. An image before the correction appears to be elongated along the axis direction if intended corrective cylinder is positive, and appears to be perpendicular to the axis direction if it is negative corrective cylinder. If the refractive error involves both spherical and cylindrical components, then the resultant image formed at the retina would have the combined effects of spherical blur and a preferential elongation.

A refractive target in accordance with certain embodiments includes thin and narrow black lines, and a base. Certain dimensions of the line and the base are described in various embodiments.

An example of a viewing target in accordance with certain embodiments is shown in FIG. 1. A thin line 110 has a length dimension substantially greater than its width. The width is chosen to be less than that of the spatial resolution limit of the eye for which the visual acuity is intended to be measured. For example, the width of the thin line can be set to 20/20 RLW, if it is used to measure visual acuity level of 20/30 or worse acuity. Since most people cannot see better than 20/10 level, it is safe to choose the width of a thin line in the inventive target to be equal to or less than 20/10 RLW (0.89 mm at 20 feet viewing, or 0.445 mm at 10 feet viewing) for a target to be used for a general population testing.

The base 120 has a thickness dimension 130, which is also configured advantageously in accordance with multiple embodiments. The base thickness is chosen in certain embodiments to be greater than visual acuity limit of the test subject. For example if a test subject has a visual acuity level of 20/15 or better, the base thickness may be set at equal to or greater than 20/15 RLW (1.33 mm at 20 feet viewing).

In accordance with certain embodiments, the width if the thin line is smaller than the test subject's RLW. A line width can be selected, for example, that is smaller than anyone's RLW in human population, such as a 20/10, or 20/8. Also, if there is a record of what a certain patient can see roughly from a previous eye exam, then the line width can be selected in accordance with the last known RLW of the test subject, at least as a starting point.

Acuity Testing

Another advantageous feature in accordance with certain embodiments is that the length of the thin line is adjustable. In one embodiment, the length of the thin line can be used to gauge the visual acuity of a test subject. One method to test the visual acuity level is to provide a long thin line attached to a base, e.g., a dark base such as a black or blue base, for the test subject to look at. In an example, as schematically illustrated in FIG. 2(A), the line width is set at less than 20/10 RLW, and the line length is set at 20/60 RLW. Since most normal functioning test subject's have vision that is better than 20/40, a test subject with such visual acuity should be able to see the thin line and the dark base. Next, the thin line is shortened as illustrated in FIG. 2(B). Then it is further shortened as shown in FIG. 2(C), where the test subject can no longer distinguish the existence of a line, or a "small tick mark" above the black base. At this point, the thin line appears to the test subject to have disappeared into the base. The RLW line length when this happens is a measure of the test subject's visual acuity. For example if the thin line disappears as the line is shortened to 20/15 RLW, the test subject has a visual acuity level of 20/15 or worse. The increment of adjustability for the line length is approximately continuous in accordance with human eye resolvability, and in practice would be limited by the display capacity of the monitor, e.g., the increment could be one pixel on the display. For higher resolution display, the increment could be two pixels or more and the increment can start out higher and be more finely adjusted as the minimum resolvable length is reached by a test subject.

An advantage of using a viewing target in accordance with certain embodiments for acuity testing is that it is a subjective and fast test that can be easily self administered. In one embodiment, the test subject can use a knob to change the length of the thin line above. The test subject is asked to turn the knob until the line disappears into the black base, stopping at exactly when it disappears. Then, the test subject can push a second button to indicate the test is finalized. A visual acuity result can then be printed out, stored or displayed on a screen for record keeping. The test subject does not need to read English letters. This target can be used by illiterate subject's, and across all languages.

As it is useful to set a generally usable width of the thin line for a general population in an example above, the base can be chosen to make such a viewing target useful, for a range in VA in test subjects from 20/10 to 20/100, for example, if the base thickness is greater than 20/100 RLW (or 8.9 mm at 20 feet viewing).

To eliminate the dependency of directional dependency, a viewing target in accordance with certain embodiments may be constructed with a series of multiple thin lines, extending from a base, in this example a round disk, or a circular area as shown in FIG. 3(A).

Now, let's continue with the dark on light, e.g., black on white scheme, and another advantageous feature in accordance with certain embodiments is that the brightness of the "white" background can be adjustable to control the luminance of the target. Through the brightness adjustment, the amount of light entering the test subject's eye is controlled, and thereby the pupil opening is controlled when such viewing target is used.

A disk, which may be a dark disk such as a black disk, is placed at the center. This central area can be used as a base of the thin lines. The boundary of the disk may be curved or may include a series of line segments or a combination thereof. The point of contact between the thin lines and the disk surface generally the disk surface perpendicular to each of thin lines in FIG. 3(A). This is advantageous to provide image diffusion between the base area and the thin line as effective as the target shown in FIG. 1. However, the line may form an acute angle with the base, and there may be multiple lines protruding from the base at different angles even when the base comprises a flat, straight surface.

The exact location of the entire target is not a limiting factor, as long as it is within the field of view of the test subject.

The exact dimension and shape of the disk at the center is also not a limiting factor of the invention. It may have a diameter from 20/25 RLW, to greater than 20/100 RLW. It can be smaller or larger. When a viewing target in accordance with certain embodiments is used at a distance 20 feet or 6 meters from the test subject, an advantageous range of the diameter of the disk may be 5 mm to 60 mm.

The length of the thin lines and the radius of the disk are scaled in certain embodiments depending on the viewing distance where the target is place from the test subject. This scaling feature may be in principle similar to that of Snellen eye chart. In its way, the letter size may be determined in relationship to the viewing distance.

In the example target shown in FIG. 3(A), the base is a disk having a radius of 20 mm, and the thin lines are 9 mm in length. The "width" of the line in the thin dimension is 0.5 mm. The thin line width can range from 0.1 mm to 2 mm, for example. The ratio of the length to the width of the thin lines ranges from 2 to 1 for the short lines, to the long thin lines with a dimensional ratio of 50 to 1. The dimensional ratio of the length to the width of the thin lines is not a limiting factor.

A typical test procedure for determining a visual acuity level of a test subject can be according to the following: A standard calibration procedure may be performed to compare the visual acuity of a standard Snellen eye chart against that of a viewing target in accordance with certain embodiments. This is recommended since the room light conditions and the viewing distance may vary from exam room to exam room. The line length of the viewing target may initially be set to 1.8 mm. This would be equivalent to a 20/20 acuity level. Now we can use this line length as a reference.

As specified with the dimensions specified for FIG. 3 (A), when that target is placed at 20 feet or 6 meters from the test subject, a person with a visual acuity level of better than 20/20 would be able to see all the thin lines "sticking" out of the central base area. Then in FIG. 3(B), the lines are shortened from 9 mm to 4 mm. Now the test subject may indicate that all the lines are still visible. Then the lines are further shortened to 2 mm. At this point, the test subject may indicate that some of the thin lines are missing around the base. FIG. 3 (D) illustrates an example of what a test subject may see of the target with six of the eight lines visible and two not visible to the test subject. The target is showing an acuity standard of 20/(2/1.89)×20, or 20/21.2. The boundary surface of the base provides for blur to wash out the short 2 mm line appearance when the line length approaches the limit of the test subject's visual acuity level. Therefore, such viewing target can be used effectively to measure the visual acuity level of a test subject. The acuity level of the test subject in this case, would be 20/21.2.

Since the entire target is compact in size, a test subject can see it in its entirety in a glance. It may be compared to looking at a single Snellen letter in a regular test eye chart. An advantage of a viewing target in accordance with certain embodiments, such as that illustrated at FIGS. 3(A) to 3(D), is that it eliminates the directional preference of Sellen letters, because it has lines pointing at the entire 360 degrees, in 45 degrees steps. The target may include more or less thin lines. The lines can be made to point in 5 degrees, 10, 15, or 30 degree steps. The angle separation between the lines is not a limitation of the invention.

One advantage of a viewing target in accordance with certain embodiments is its ability to measure an approximately continuously variable length (limited only by the pixel size of a display or by an exam room schedule limitation on number of slides used, and certainly not nearly as limited by discrete step size as a Snellen eye chart of 20/20, 20/40, etc. A viewing target in accordance with certain embodiments may be displayed using an electronic computer monitor, television screens, LED, LCD, Plasma, or electron gun screens, or a projection screen, or a non-electronic display such as a series of slides, cards, wall hangings, or it may be a series of images, printed on paper, or displayed through electronic monitor. The line length is easily adjustable using computer generated graphics. The intensity of the light background may be adjustable by the brightness control of the computer or TV monitor or using a computer program and the click and/or drag of a mouse.

Figure 4B:
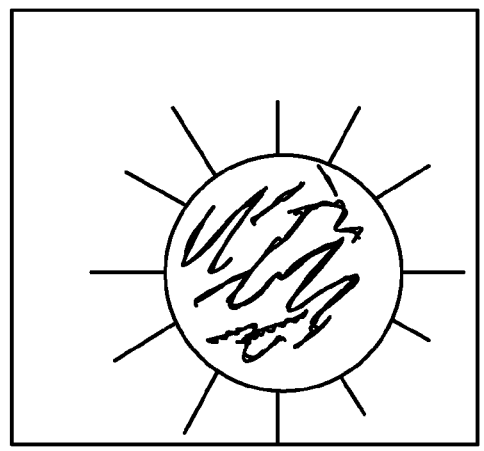
FIG. 4b schematically illustrates a viewing target in accordance with certain embodiments including a circular base connected to multiple lines.

The number of thin lines and the angular arrangement of the lines around the base are not limiting factors. A sufficient number of lines is desired in certain embodiments to cover the orientation ranging from 0 degree to 180 degrees as shown in FIG. 4(A), although even the single line embodiment of FIG. 1 may be used advantageously in embodiments whether the viewing target of FIG. 1 is rotatable to change the angle of the line on a display or not. An example of five lines covering 45 degree increments from 0 to 180 degrees may be used. FIG. 4(A) shows seven angularly equally spaced lines each covering 30 degree angle steps from zero to 180 degrees. Typical target may contain 5 to 26 lines per 180 degrees. But the angular separation may be as small as 2 degree increments. It is sufficient to show the target with thin lines covering only a semi-circular base as shown in FIG. 4(A), since it covers 0 to 180 degrees. However, it may be desired to have a more symmetric and comfortable viewing target that includes lines protruding over an entire circular area from 0 to 360 degrees, as shown in FIG. 4(B).

So far, the viewing target has been illustrated with a white background, thin black lines and a black base. However this "black on white" scheme is not a limiting factor. Alternative, one can have the viewing target in "reverse color", namely, thin white lines and white base on a black ground, with a white disk base area. Furthermore, the background and the lines/base may have colors such as yellow, green, or red, etc. The color of the lines, base, and its background is not a limiting factor. The brightness level of a white or otherwise light background may be controlled to display in various gray levels.

Furthermore, the contrast of the black line against the white background may also be adjustable. If one defines a 100% contrast level as a full black on a 100% brightness white background, then one may increase the brightness of the line to 50% full brightness level, on a 100% brightness white background and define that line as having a 50% contrast level. Now that line is more like a gray line rather than a black line. In this way, one may adjust the contrast level of the line to perform contrast acuity testing.

A contrast acuity test may be generally considered more revealing about the quality of vision than a high contrast (100% contrast) acuity test. One may use a viewing target in accordance with certain embodiments to conduct a variable contrast acuity test. To do that, one may first lower the contrast level of the line to a desirable level, for example at 12%, or a 5% contrast. Then this lower contrast target may be used to conduct an acuity test the same way as using 100% contrast lines, as described above. The contrast level of the lines may have a range from 1% to 100%.

Viewing Target as Used in Refraction Procedures

A viewing target in accordance with certain embodiments is more advantageous than a Snellen letter eye chart, particularly when it is used to refract, namely to find the best refraction end points for a test subject's sphere, cylinder and/or axis angle.

With a proper arrangement of the thin lines, with equally and angularly spaced lines, for example, the target eliminates the angular asymmetry or the angular preference of a letter eye chart. Such target is sensitive for cylinder errors and at cylindrical axis.

The thin lines are sensitive to the effects of spherical error, or defocusing errors. Their widths are smaller than those of a typical standard Snellen letter. Over-minusing is a condition that is often encountered when Snellen eye charts are used. Due to the thin line thickness of the lines of the viewing target in accordance with certain embodiments, there is no demagnification effect in the line width dimension, which could happen with Snellen letters. When too much minus spherical power is added to the refraction correction, the size of the letters of the Snellen eye chart appear to be darker due to the reduction in letter size with higher minus power, leading to a false refraction end point. Since the line is thin, there is very little effect to produce a thinner line, or "darker" appearance, as in the case with Snellen letters. Therefore, a viewing target in accordance with certain embodiments does not favor over-minusing as would be when using a Snellen eye chart.

Figure 5A:
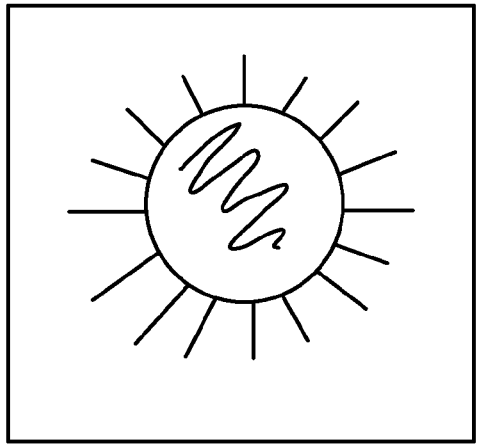
FIGS. 5a-5d schematically illustrate elongating a viewing target and shortening the lines of the viewing target in accordance with certain embodiments to measure residual cylinder error.
Figure 5B:
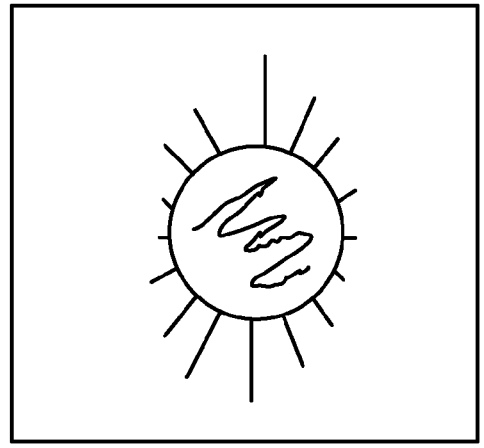
Figure 5C:
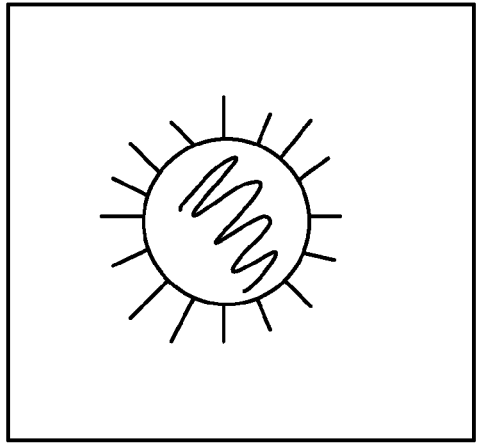
Figure 5D:
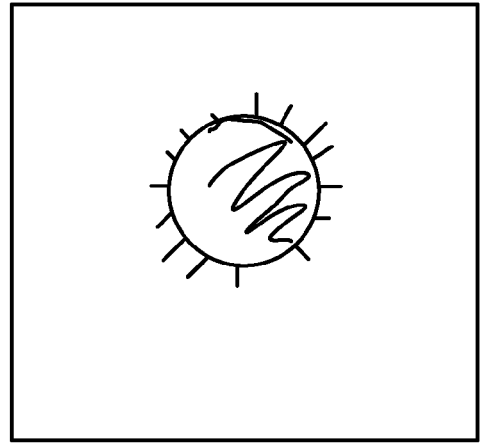

When there is residual cylinder error, a target as shown in FIG. 5(A) may appear to the test subject as shown in FIG. 5(B), in which some of the lines would disappear while other lines at 90 degree from them stay visible and appear more elongated. When cylinder error is corrected, the thin lines appear equally visible and focused as shown in FIG. 5(A). Therefore, one way to determine if there are any residual cylinder errors is to shorten the thin lines from FIG. 5(A), to FIG. 5(C), then to FIG. 5(D), and ultimately to a shortened length when all lines disappear almost simultaneously at about the same line length. Snellen eye charts cannot provide such a definitive end point by looking at the letters.

To find an axis angle of a cylinder error, one could use the partial disappearance of the lines to determine which angle is closer to the axis end point, namely, at the corrected axis angle. For example, if the target appears to the test subject as shown in FIG. 5(A) at axis angle X, as compared to an image of FIG. 5(B) formed at a second axis angle Y. In this case, the corrected axis angle is closer to the angle X as compared to angle Y. By comparing the image quality of a viewing target in accordance with certain embodiments at two cylinder angles under consideration, one can use the quality of the image of all lines to determine which one is more symmetric and more focused, thereby approaching the optimal end point for the cylinder correction.

Figure 6:
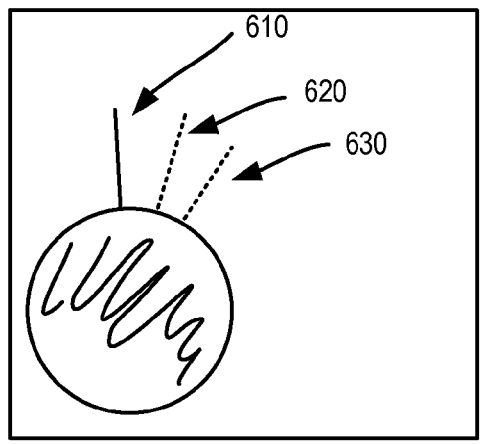
FIG. 6 schematically illustrates moving a line around a circular base to determine an axis angle of a cylinder error in accordance with certain embodiments.

There are other variations of viewing targets in accordance with alternative embodiments. For example, one thin line may be made to appear at a time, as illustrated at FIG. 6. Using an electronic display, one may display only one line at any instant in this embodiment. The position of that line then shifts to the next incremental angle as illustrated at FIG. 6. A line 610 first appears. Then line 610 disappears, and line 620 appears at 15 degrees, for example, angularly spaced from line 610. Next the line 620 disappears, and new line 630 appears at another 15 degrees from line 620. This disappearance and appearance sequence continues with a new line at an angular increment, as new lines appear around the base disk, as illustrated in FIG. 6. Each of the lines may appear for a duration ranging 0.01 seconds to 2 seconds. The stay on time of the line is generally not a limitation here. The angular separation of 15 degrees here is mere exemplary, and not a limitation either. The angular steps may range from 2 degrees to 45 degrees.

Figure 7:
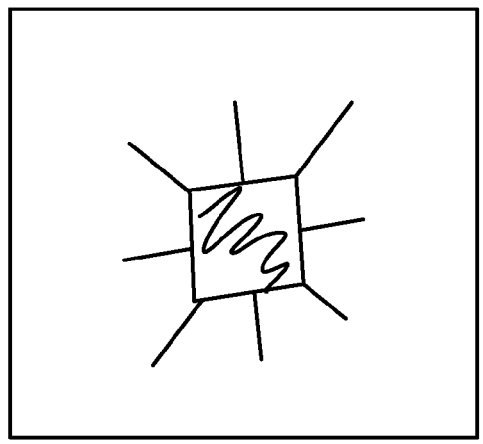
FIGS. 7, 8 and 9 schematically illustrates alternative viewing targets with non-circular bases in accordance with certain alternative embodiments.
Figure 9:
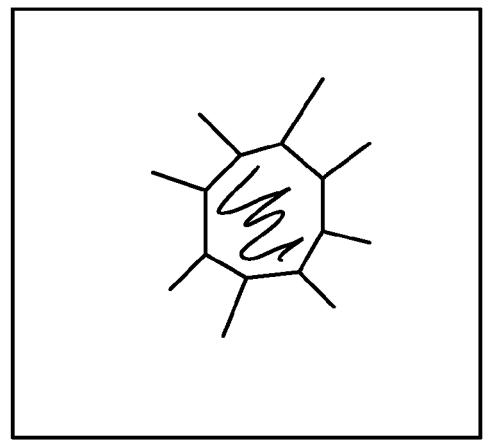
Figure 8:
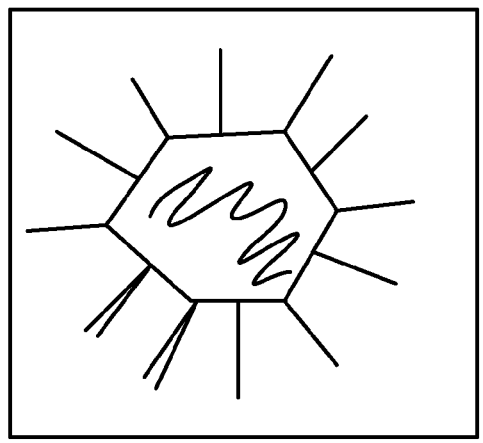

Another variation can be that the base area is a square as shown in FIG. 7, or a hexagon as in FIG. 8, or an octagon as in FIG. 9, or some other polygon or curved regular or irregular shape. The thin lines radiate from the base edges. The square can be changed to a rectangle. Round disks of the base may be substituted by an oval base area. The exact shape of the base is also not a limiting factor.

The described embodiments are merely illustrative and the invention is not limited to the specifically-described examples. Instead, the invention is set forth in the claims and includes structural and functional equivalents thereof.

What is claimed is:

1. A tangible medium displaying a viewing target for a visual acuity or a refraction measurement of a test subject, wherein the viewing target comprises:

(a) at least one line comprising a width dimension that is below a resolution limit width (hereinafter "RLW") of a test subject visual acuity, and an adjustable length dimension that is initially set at greater than the RLW of the test subject visual acuity and is adjustable to one or more reduced lengths including at or near the RLW of the test subject visual acuity; and (b) a base, comprising at least one or more further lines including at least one of said one or more further lines approximately intersecting the at least one line, wherein the viewing target includes an elliptical, circular, semi-circular, oval, square, rectangle, hexagon, octagon or other polygon, or a curved regular or irregular shape and the base having a thickness along the direction of the length of the at least one line that is greater than the RLW of the test subject visual acuity.

2. The tangible medium of claim 1, whereby in performing a visual acuity measurement of a test subject, the length dimension of the line is adjustable in increments small enough to effectively approximate the visual acuity of the test subject by determining a shortest resolvable line and a next smaller line that is not resolvable by the test subject.

3. The tangible medium of claim 2, wherein the increments of the adjustable length of the line comprise an integer multiple of one display pixel.

4. The tangible medium of claim 1, wherein the line and the base each comprise black color, and a background against which the target is displayed comprises white or gray color, or a combination thereof.

5. The tangible medium of claim 1, wherein the line and the base comprise white or gray color, or a combination thereof, and a background against which the target is displayed comprises black color.

6. The tangible medium of claim 1, wherein colors of the line and base and background against which the target is displayed are selectable.

7. The tangible medium of claim 1, wherein the width of the line comprises less than 20/10 RLW.

8. The tangible medium of claim 1, wherein the length of the line comprises greater than 20/40 RLW.

9. The tangible medium of claim 1, wherein the thickness of the base comprises greater than 20/40 RLW.

10. The tangible medium of claim 1, comprising a plurality of lines differing in their length or direction, or combinations thereof.

11. The tangible medium of claim 10, wherein the base comprises a polygon and each of the lines protrude from the base.

12. The tangible medium of claim 10, comprising at least five lines protruding from the base angularly spaced at approximately equal angles apart, wherein the angles range from 2 degrees to 45 degrees.

13. The tangible medium of claim 10, wherein each of the lines are equal in length and adjustable.

14. The tangible medium of claim 11, wherein the base comprises a circular shape.

15. The tangible medium of claim 10, wherein the target is adjustably elongatable.

16. The tangible medium of claim 4, wherein a contrast level of the at least one line is adjustable in a range between 1% and 100%.

17. The tangible medium of claim 1, wherein the viewing target is displayable on a computer monitor, other electronic screen, or non-electronic screen including, cards, wall hangings, projector screen.

18. The tangible medium of claim 1, wherein the base comprises a circular shape, and the viewing target is adjustable for displaying in temporal increments a line protruding from the base at different angles.

19. The tangible medium of claim 18, wherein the different angles comprise increments between 2 degrees and 45 degrees.

20. The tangible medium of claim 18, wherein the temporal increments comprise 0.01 seconds to 2 seconds.

21. The tangible medium of claim 1, wherein the line and base comprise a same color.

22. A visual acuity measurement system, comprising:
   (a) a display for showing a viewing target as in any of claims 1-21;
   (b) a machine coupled with the display and configured to adjust the viewing target on the display during a visual acuity measurement of a test subject; and
   (c) a calculator or look-up table, or both, for determining the visual acuity of the test subject based on the adjusting of the viewing target.

23. A method of determining a visual acuity level of a test subject, comprising reducing a length of at least one line in a viewing target until the test subject indicates that the line has disappeared into a base, wherein the viewing target comprises:
   (a) the at least one line comprising a width dimension that is below a resolution limit width (hereinafter "RLW") of a test subject visual acuity, and an adjustable length dimension that is initially set at greater than the RLW of the test subject visual acuity and is adjustable to one or more reduced lengths including at or near the RLW of the test subject visual acuity; and
   (b) the base, comprising at least one or more further lines including at least one of said one or more further lines approximately intersecting the at least one line, wherein the viewing target includes an elliptical, circular, semi-circular, oval, square, rectangle, hexagon, octagon or other polygon, or a curved regular or irregular shape and the base having a thickness along the direction of the length of the at least one line that is greater than the RLW of the test subject visual acuity, and
   (c) whereby in performing a visual acuity and refraction measurement of the test subject, the length dimension of the line is adjustable in increments small enough to effectively approximate the visual acuity of the test subject by determining a shortest resolvable line and a next smaller line that is not resolvable by the test subject.

24. The method of claim 23, comprising a plurality of lines differing in their length or direction, or combinations thereof.

25. The method of claim 23, wherein the base comprises a polygon and each of the lines protrude from the base.

26. The method of claim 24, comprising at least five lines protruding from the base angularly spaced at approximately equal angles apart, wherein the angles range from 2 degrees to 45 degrees.

27. The method of claim 24, wherein each of the lines are equal in length and adjustable.

28. The method of claim 24, wherein the base comprises a circular shape.

29. The method of claim 24, wherein the target is adjustably elongatable.

30. A method of determining a refraction error comprising determining a quality of an image of a viewing target, wherein the viewing target comprises:
   (a) at least one line comprising a width dimension that is below a resolution limit width (hereinafter "RLW") of a test subject visual acuity, and an adjustable length dimension that is initially set at greater than the RLW of the test subject visual acuity and is adjustable to one or more reduced lengths including at or near the RLW of the test subject visual acuity; and
   (b) a base, connecting one end of the line, the base comprising at least one or more further lines including at least one of said one or more further lines approximately intersecting the at least one line, wherein the viewing target includes an elliptical, circular, semi-circular, oval, square, rectangle, hexagon, octagon or other polygon, or a curved regular or irregular shape and the base having a thickness along the direction of the length of the at least one line that is greater than the RLW of the test subject visual acuity.

31. The method of claim 30, further comprising adjusting the length dimension of the line in increments small enough to effectively approximate the visual acuity of the test subject by determining a shortest resolvable line and a next smaller line that is not resolvable by the test subject.

32. The method of claim 30, wherein the target comprising a plurality of lines differing in their length or direction, or combinations thereof.

33. The method of claim 32, wherein the base comprises a circular or a polygon and each of the lines protrude from the base.

34. The method of claim 32, comprising at least five lines protruding from the base angularly spaced at approximately equal angles apart, wherein the angles range from 2 degrees to 45 degrees.

35. The method of claim 32, wherein each of the lines are equal in length and adjustable.

36. The method of claim 32, wherein the target is adjustably elongatable.

37. A method of determining a refraction error comprising reducing a length of at least one line in a viewing target until a test subject indicates that the line has disappeared into a base, wherein the viewing target comprises:
   (a) at least one line comprising a width dimension that is below a resolution limit width (hereinafter "RLW") of a test subject visual acuity, and an adjustable length dimension that is initially set at greater than the RLW of the test subject visual acuity and is adjustable to one or more reduced lengths including at or near the RLW of the test subject visual acuity; and
   (b) a base, comprising at least one or more further lines including at least one of said one or more further lines approximately intersecting the at least one line, wherein the viewing target includes an elliptical, circular, semi-circular, oval, square, rectangle, hexagon, octagon or other polygon, or a curved regular or irregular shape and the base having a thickness along the direction of the length of the at least one line that is greater than the RLW of the test subject visual acuity, and
   (c) whereby in performing a visual acuity and refraction measurement of the test subject, the length dimension of the line is adjustable in increments small enough to effectively approximate the visual acuity of the test subject by determining a shortest resolvable line and a next smaller line that is not resolvable by the test subject.

38. The method of claim 37, wherein the target comprises a plurality of lines differing in their length or direction, or combinations thereof.

39. The method of claim 37, wherein the base comprises a circular shape area or a polygon and each of the lines protrudes from the base.

40. The method of claim 38, comprising at least five lines protruding from the base angularly spaced at approximately equal angles apart, wherein the angles range from 2 degrees to 45 degrees.

41. The method of claim 38, wherein each of the lines are equal in length and adjustable.

42. The method of claim 38, wherein the target is adjustably elongatable.

* * * * *